United States Patent [19]

Butterfield

[11] 4,439,187
[45] Mar. 27, 1984

[54] HYPODERMIC SYRINGE

[75] Inventor: Ida M. Butterfield, Santa Maria, Calif.

[73] Assignee: Butterfield Group, Santa Maria, Calif.

[21] Appl. No.: 364,006

[22] Filed: Mar. 31, 1982

[51] Int. Cl.³ .............................................. A61M 5/00
[52] U.S. Cl. ..................................................... 604/111
[58] Field of Search ................... 604/111, 93, 38, 183, 604/218, 219, 220, 221, 222, 228, 110

[56] References Cited

U.S. PATENT DOCUMENTS

| | | | |
|---|---|---|---|
| 1,747,243 | 2/1930 | Hoskins | 128/218 D |
| 2,020,828 | 11/1935 | Goldberg | 128/218 D |
| 3,126,004 | 3/1964 | Sarnoff | 604/111 |
| 3,366,113 | 1/1968 | Hobbs | 128/218 D X |
| 3,485,239 | 12/1969 | Vanderbeck | 128/218 S |
| 3,677,247 | 7/1972 | Brown | 128/218 S |
| 3,754,644 | 8/1973 | Hampel | 128/218 S |
| 3,941,129 | 3/1976 | Pleznac | 128/218 P |
| 4,014,331 | 3/1977 | Head | 128/224 |
| 4,048,997 | 9/1977 | Raghavachari et al. | 128/218 R |

FOREIGN PATENT DOCUMENTS 554179   7/1932   Fed. Rep. of Germany ...... 604/232

*Primary Examiner*—John D. Yasko
*Attorney, Agent, or Firm*—Daniel C. McKown

[57] ABSTRACT

An improvement for use with a particular type of hypodermic syringe having a non-retractable stopper located ahead of the drive piston so that the position of the non-retractable stopper indicates the extent to which the drive piston has been advanced. The improvement is a substantially opaque sleeve, or coating applied to the transparent tubular body of the syringe, or a substantially opaque section of the tubular body itself, that is positioned to obstruct the user's view of the non-retractable stopper when the latter is in its original position as supplied by the manufacturer. The front end of the sleeve, coating, or section coincides axially with the front end of the non-retractable stopper so that any forward movement of the non-retractable stopper will expose to view a portion of the non-retractable stopper.

11 Claims, 6 Drawing Figures

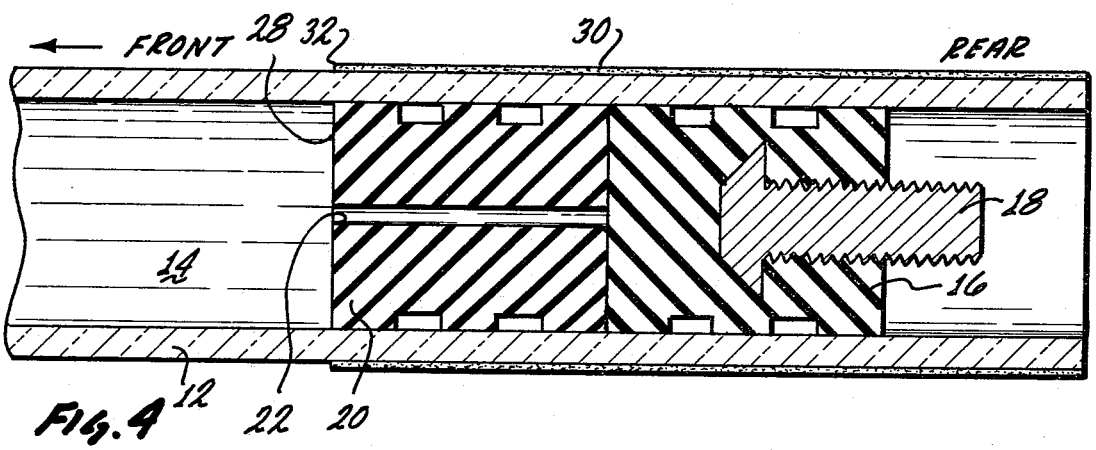
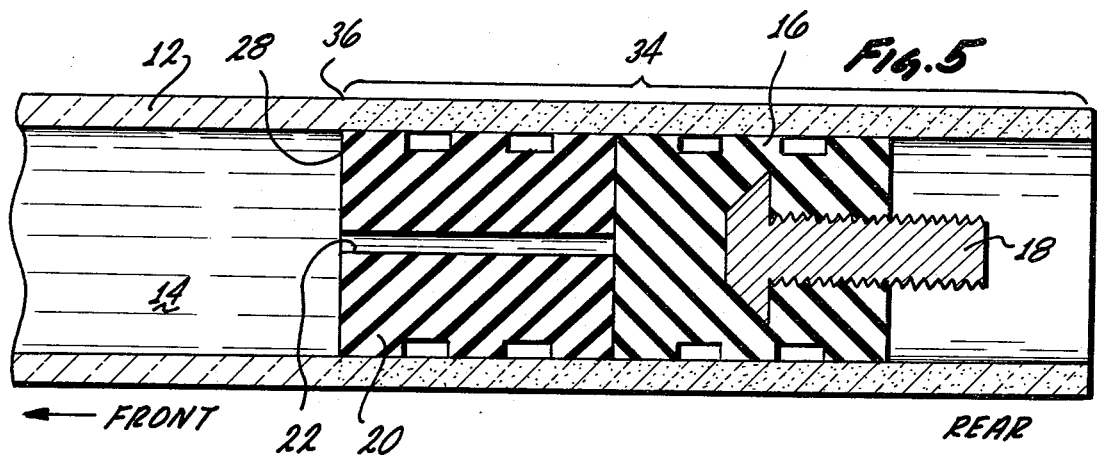
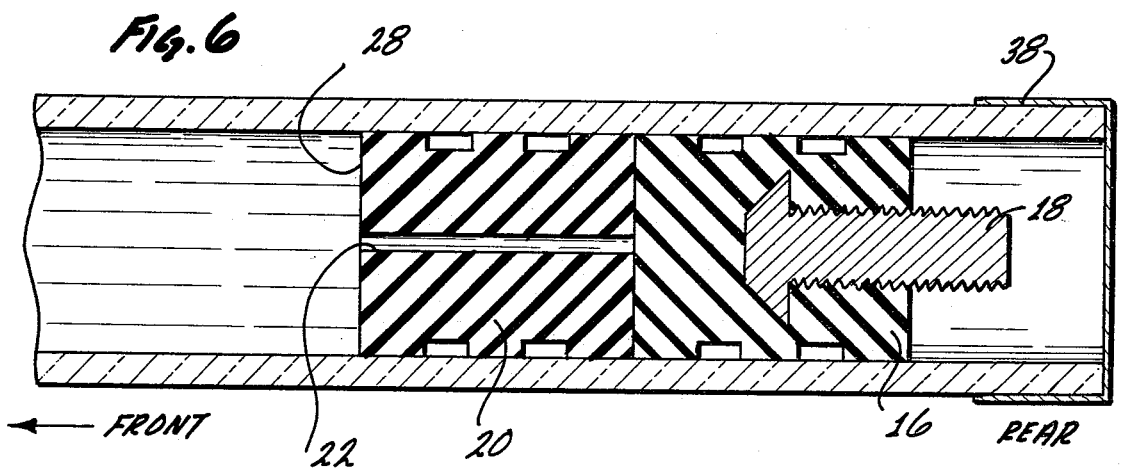

HYPODERMIC SYRINGE

BACKGROUND OF THE INVENTION

1. Field of the Invention

The present invention is in the field of medical articles and more specifically is an improvement to a hypodermic syringe for the purpose of making the syringe more tamper-resistant.

2. The Prior Art

The present invention is an improvement to a hypodermic syringe of the type described in U.S. Pat. No. 3,941,129, issued Mar. 2, 1976 to Ida M. Pleznac, the present inventor. The invention of that patent is illustrated in FIG. 1 and FIG. 2 herein. These figures show the end of a hypodermic syringe that is opposite the end from which the needle extends.

In common with other hypodermic syringes, all of the syringes shown herein in FIGS. 1-5 include a tubular member 12, typically made of a transparent material, such as glass, and having a constant cross-section. The tubular member 12 contains the fluid 14 to be injected. The fluid is expressed from the syringe by applying a force to the drive piston 16, the force being directed to the left in FIGS. 1-5, and being applied by an actuator rod (not shown) which the user screws onto the screw 18 that is embedded in the drive piston 16. The drive piston 16 is made of a resilient material, such as a soft rubber, so that it will maintain a sealing engagement with the inside wall of the tubular member 12 as the drive piston 16 is forced to the left as viewed in FIGS. 1-5.

The invention described in the aforementioned U.S. Pat. No. 3,941,129 differs from previous hypodermic syringes in having a non-retractable stopper 20 within the tubular member 12 and to the left of the drive piston 16. The non-retractable stopper 20 includes a longitudinal passage 22 for the fluid 14 to flow through. The non-retractable stopper is not connected to the drive piston 16, although they may be in contact sometimes.

FIG. 1 shows the syringe as it would be initially supplied from the manufacturer, but prior to use. Note that the non-retractable stopper 20 is in contact with the drive piston 16. In use, the drive piston 16 is pushed to the left as viewed in the figures, driving before it the non-retractable stopper 20, as fluid is expressed from the syringe. The drive piston 16 may be left at the position to which it had been advanced leftward, or alternatively, the drive piston 16 may be retracted to the right, particularly if the fluid originally expressed is to be replaced by a substitute fluid. Friction holds the non-retractable stopper 20 at the position of its greatest leftward advance within the tubular member 12 even when the drive piston 16 is retracted, as shown in FIG. 2. The space between the drive piston 16 and the non-retractable stopper 20 is filled by a flow of fluid 14 through the longitudinal passage 22. All of the syringes shown in FIGS. 1-5 herein work in this same way.

Clearly, the use of the non-retractable stopper 20 is an improvement over the previous art because it enables a user to determine whether a substantial amount of fluid has been removed or has been removed and replaced. However, if only a rather small amount of fluid has been removed, discovery of the prior use of the syringe is less likely. The present invention is a simple modification of the improved syringe shown in FIGS. 1 and 2. This modification has as its purpose to facilitate detection of the removal of even relatively small amounts of fluid from the syringe.

SUMMARY OF THE INVENTION

The difficulty which most users have in detecting the removal of only a relatively small amount of fluid from the hypodermic syringe of FIGS. 1 and 2 is remedied by the present invention. In accordance with the present invention, there is provided an opaque layer which surrounds the tubular member and which obscures from view the non-retractable stopper provided the non-retractable stopper is in its original position. If any of the fluid has been removed from the syringe, the non-retractable stopper will have been moved to the left of its original position and hence will become visible to the user. In a preferred embodiment of the invention, the non-retractable stopper is made of a visually-conspicuous material, such as a brightly colored material, so as to enhance the visibility of it to the user.

The novel features which are believed to characterize the invention, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 4 is a fractional cross-sectional view similar to that of FIG. 3 and showing a second preferred embodiment of the present invention, FIG. 5 is a fractional cross-sectional view similar to that of FIG. 3 and showing a third preferred embodiment of the syringe of the present invention; and FIG. 6 is a fractional cross-sectional view similar to that of FIG. 3 and showing another embodiment of the syringe of the present invention.

DETAILED DESCRIPTION

Figure 1:
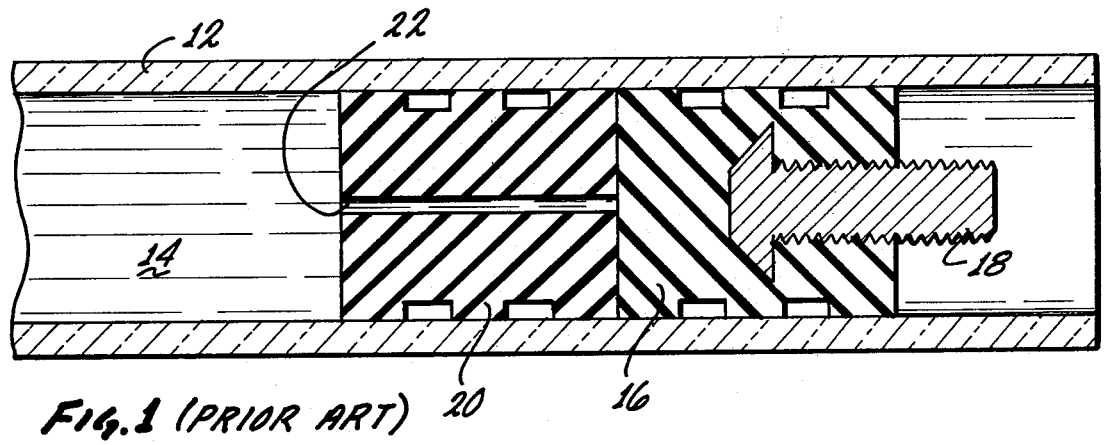
FIG. 1 is a fractional cross-sectional view in a plane containing the longitudinal axis of a syringe of the prior art, in the condition in which that syringe is normally supplied to the user.
Figure 2:
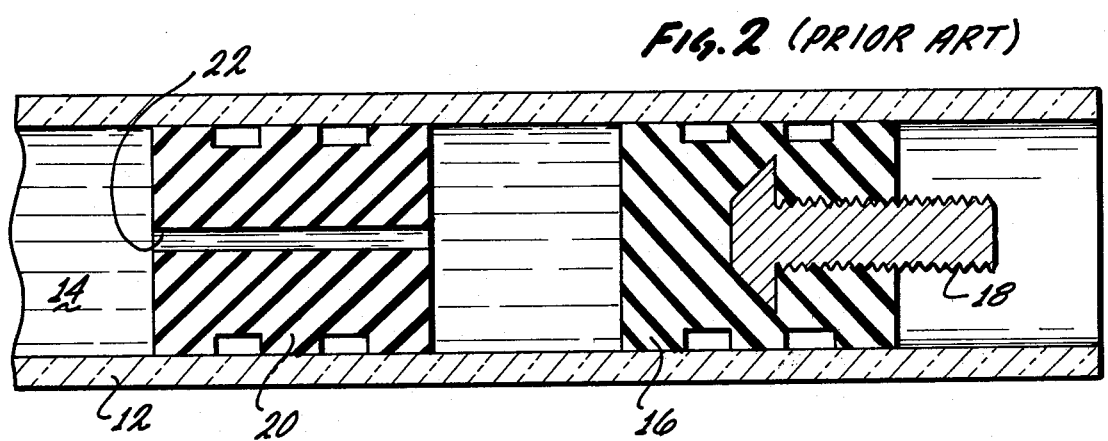
FIG. 2 is a fractional cross-sectional view similar to that of FIG. 1 and showing the configuration of the prior art syringe after some fluid has been removed from it and replaced.
Figure 3:
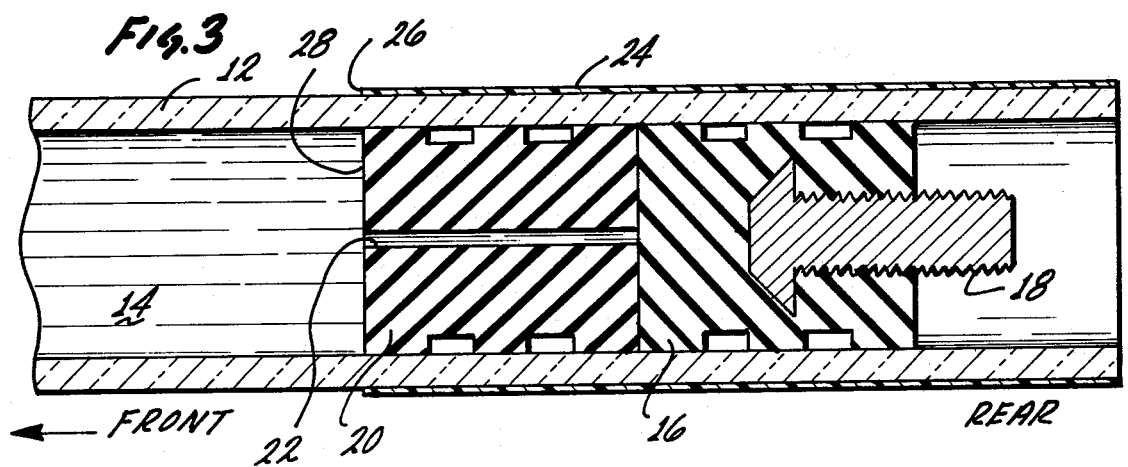
FIG. 3 is a fractional cross-sectional view of an improved hypodermic syringe taken in a plane containing the longitudinal axis of the syringe and showing a first preferred embodiment of the present invention.

In the first preferred embodiment shown in FIG. 3, a substantially opaque sleeve 24 is provided on the outside surface of the tubular member 12. The sleeve 24 may be made of any suitable substantially opaque material, including by way of example, a heat-shrinkable tubing of the type used in electronic manufacturing. Alternatively, the sleeve 24 may be bonded to the tubular member 12 by an adhesive. In yet another variation, the sleeve 24 may be maintained at a higher temperature than the tubular member 12 prior to being applied to the tubular member, so that the tubular member 12 and the sleeve 24 reach substantially the same temperature, the sleeve 24 will be held securely in place on the tubular member 12 by thermal contraction. It is desirable that the front end 26 of the sleeve 24 be located axially at substantially the same location as the front end 28 of the non-retractable stopper 20, so as to obstruct the user's view of the non-retractable stopper 20 when the syringe is in mint condition. It is desirable that the non-retractable stopper 20 be made of a brightly-colored material so as more readily to draw the user's attention to any portion of the non-retractable stopper 20 that may be exposed beyond the front end 26 of the sleeve 24.

In still another variation, the sleeve 24 extends only from the front end 28 of the non-retractable stopper to the rear end of the non-retractable stopper so that the user can verify that no space exists initially between the non-retractable stopper 20 and the drive piston 16. Such a space would indicate that fluid has been added to the syringe.

The same considerations apply to FIG. 4 in which is shown a second preferred embodiment of the present invention. In this embodiment, the sleeve 24 of FIG. 3 is replaced by the coating 30. The coating 30 is substantially opaque and serves the same purpose as the sleeve 24 of FIG. 3. It is contemplated that the coating 30 would be applied to the tubular member 12 in a liquid form which would subsequently dry and harden to form a dry coating that adheres to the tubular member 12. The coating 30 might, for example, be a black paint. In another variation, the coating 30 is a fired enamel that is fused onto the tubular member 12. In this second preferred embodiment shown in FIG. 4, the front end 32 of the coating is substantially at the same axial location as the front end 28 of the non-retractable stopper 20. As was mentioned in connection with FIG. 3, the coating 30 may extend only to the rear end of the non-retractable stopper 20, or alternatively, the coating may extend beyond the rear end of the non-retractable stopper.

FIG. 5 shows a third preferred embodiment in which neither a sleeve nor a coating is used. Instead, a section 34 of the tubular member 12 is formed of a substantially opaque material, for example, a non-transparent glass or plastic. As was the case in FIGS. 3 and 4, it is desirable that the front end 36 of the opaque section 34 be located substantially at the same axial position as the front end 28 of the non-retractable stopper. Also, the present invention encompasses both the option of terminating the opaque section at the rear end of the non-retractable stopper and the option of extending the opaque section beyond (to the right in FIG. 5) the rear end of the non-retractable stopper.

In FIGS. 3, 4 and 5 the front end of the opaque portion constitutes a fixed point along the tubular member, relative to which the slightest movement of the non-retractable stopper can be detected.

In a further variation on the embodiments shown in FIGS. 3, 4, and 5, the rear end of the opaque portion coincides axially with the rear end of the drive piston 16, and the drive piston 16 is made of a brightly-colored material, preferably of a color different from that used for the non-retractable stopper. The purpose of this variation is to permit any rearward movement of the drive piston 16 to be detected. Such rearward motion, if present, would indicate that fluid has been added to the syringe.

Finally, FIG. 6 shows still another embodiment of the present invention. In the embodiment of FIG. 6, the rear end of the tubular member 12 is sealed by a cap 38 of a metallic foil or other suitable opaque membrane, which is bonded to the outside surface of the tubular member 12.

In a variation of the embodiment of FIG. 6, the cap 38 of metallic foil extends forward from the rear end of the tubular member and terminates at the front end 28 of the non-retractable stopper 20, thereby serving the same purpose as the sleeve 24 of FIG. 3.

The drive piston 16 cannot be pushed forward unless the object, such as an actuator rod, used for pushing it forward has first penetrated the cap 38. Perforation of the cap 38 can be readily detected by inspection. Clearly, this use of the cap 38 is not limited to syringes having a non-retractable stopper.

The foregoing detailed description illustrates several embodiments of the invention, and it is to be understood that additional variations thereof will be obvious to those skilled in the art. The embodiments described herein together with those additional variations are considered to be within the scope of the invention.

What is claimed is:

1. An improvement for use in a hypodermic syringe cartridge of the type having a front end to which a hypodermic needle is normally attached and having a rear end opposite the front end, and in which a non-retractable stopper having a longitudinal passage, a front end and a rear end is located within a tubular member in front of a drive piston having a front end and a rear end, the cartridge normally supplied with the rear end of the non-retractable stopper substantially in contact with the front end of the drive piston near the rear end of the cartridge, the improvement comprising: substantially opaque means being a permanent part of the tubular member of the hypodermic syringe cartridge as supplied for use and so located axially as to obstruct from view the non-retractable stopper when the non-retractable stopper is in its original position and having a front end that terminates at the front end of the non-retractable stopper when the non-retractable stopper is in its original position so that any forward movement of said non-retractable stopper will expose to view a portion of the non-retractable stopper.

2. The improvement of claim 1 wherein said substantially opaque means extends rearwardly only so far as the rear end of the non-retractable stopper so that any space between the non-retractable stopper and the drive piston can be seen.

3. The improvement of claim 1 wherein said substantially opaque means extends rearwardly only so far as the rear end of the drive piston when the drive piston is in its original position so that any rearward movement of said drive piston will expose to view a portion of the drive piston.

4. The improvement of claim 1 wherein said substantially opaque means is a sleeve encircling the tubular member.

5. The improvement of claim 1 wherein said substantially opaque means is a coating applied to the tubular member.

6. The improvement of claim 1 wherein said substantially opaque means is a substantially opaque section of the tubular member.

7. In a tamper-resistant hypodermic syringe cartridge of the type in which a fluid is expressed when a user advances a drive piston within a transparent tubular member from an original position near one end of the tubular member, and in which a non-retractable stopper having a longitudinal passage is pushed along within the tubular member ahead of the drive piston, and in which the non-retractable stopper is not connected to the drive piston so that when the user retracts the drive piston, the non-retractable stopper remains at its most advanced position to serve as a warning that fluid has been removed from the hypodermic syringe, the improvement comprising:

a substantially opaque sleeve permanently affixed to the tubular member and surrounding the tubular member near said one end and concealing said non-retractable stopper when said non-retractable stopper is in its original position so that said non-retractable stopper becomes visible only when said non-retractable stopper has been advanced from its original position.

8. In a tamper-resistant hypodermic synringe cartridge of the type in which a fluid is expressed when a user advances a drive piston within a transparent tubular member from an original position near one end of the tubular member; and in which a non-retractable stopper having a longitudinal passage is pushed along within the tubular member ahead of the drive piston, and in which the non-retractable stopper is not connected to the drive piston so that when the user retracts the drive piston, the non-retractable stopper remains at its most advanced position to serve as a warning that fluid has been removed from the hypodermic syringe, the improvement comprising:

a substantially opaque coating on the tubular member near said one end concealing said non-retractable stopper when said non-retractable stopper is in its original position so that said non-retractable stopper becomes visible only when said non-retractable stopper has been advanced from its original position.

9. In a tamper-resistant hypodermic syringe cartridge of the type in which a fluid is expressed when a user advances a drive piston within a transparent tubular member from an original position near one end of the tubular member; and in which a non-retractable stopper having a longitudinal passage is pushed along within the tubular member ahead of the drive piston, and in which the non-retractable stopper is not connected to the drive piston so that when the user retracts the drive piston, the non-retractable stopper remains at its most advanced position to serve as a warning that fluid has been removed from the hypodermic syringe, an improved tubular member comprising:

a first tubular section of a transparent material;
a second tubular section of a substantially opaque material, said second tubular section affixed end-to-end to said first tubular section and hiding from view the non-retractable stopper when the latter is in its original position, but so located that even a slight advancement of the non-retractable stopper will render visible a portion of the non-retractable stopper.

10. In a tamper-resistant hypodermic syringe cartridge of the type in which a fluid is expressed when a user advances a drive piston within a transparent tubular member from an original position near one end of the tubular member, and in which a non-retractable stopper having a longitudinal passage is pushed along within the tubular member ahead of the drive piston, and in which the non-retractable stopper is not connected to the drive piston so that when the user retracts the drive piston, the non-retractable stopper remains at its most advanced position to serve as a warning that fluid has been removed from the hypodermic syringe, the improvement comprising:

an opaque cap being a permanent part of the tubular member of the hypodermic syringe cartridge as supplied for use, covering said one end of the tubular member and surrounding the tubular member near said one end and extending to conceal said non-retractable stopper when said non-retractable stopper is in its original position so that said non-retractable stopper becomes visible only when said non-retractable stopper has been advanced from its original position.

11. The improvement of claim 10 wherein said opaque cap consists of a metallic foil.

* * * * *